(12) United States Patent
Radtke

(10) Patent No.: US 9,089,488 B2
(45) Date of Patent: Jul. 28, 2015

(54) METHOD FOR MANUFACTURING MEDICINAL COMPOUNDS CONTAINING DABIGATRAN

(71) Applicant: Guido Bernhard Edmund Radtke, Ockenheim (DE)

(72) Inventor: Guido Bernhard Edmund Radtke, Ockenheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 107 days.

(21) Appl. No.: 13/898,741

(22) Filed: May 21, 2013

(65) Prior Publication Data

US 2013/0251811 A1 Sep. 26, 2013

Related U.S. Application Data

(63) Continuation of application No. 13/003,645, filed as application No. PCT/EP2009/058900 on Jul. 13, 2009, now abandoned.

(30) Foreign Application Priority Data

Jul. 14, 2008 (EP) ..................................... 08160335

(51) Int. Cl.
| | | |
|---|---|---|
| A61K 31/4439 | (2006.01) | |
| A61K 9/10 | (2006.01) | |
| A61K 9/14 | (2006.01) | |
| A61K 9/16 | (2006.01) | |
| A61K 9/48 | (2006.01) | |
| A61K 9/50 | (2006.01) | |

(52) U.S. Cl.
CPC ............... *A61K 9/1682* (2013.01); *A61K 9/485* (2013.01); *A61K 9/4816* (2013.01); *A61K 9/4866* (2013.01); *A61K 9/5078* (2013.01); *A61K 31/4439* (2013.01)

(58) Field of Classification Search
None
See application file for complete search history.

(56) References Cited

U.S. PATENT DOCUMENTS

| 4,145,308 | A | | 3/1979 | Simoneau et al. |
| 4,191,741 | A | | 3/1980 | Hudson et al. |
| 5,422,121 | A | * | 6/1995 | Lehmann et al. ............. 424/464 |
| 6,087,380 | A | | 7/2000 | Hauel et al. |
| 6,414,008 | B1 | | 7/2002 | Hauel et al. |
| 6,469,039 | B1 | | 10/2002 | Hauel et al. |
| 6,710,055 | B2 | | 3/2004 | Hauel et al. |
| 7,202,368 | B2 | | 4/2007 | Zerban et al. |
| 7,459,566 | B2 | | 12/2008 | Zerban et al. |
| 7,880,016 | B2 | | 2/2011 | Zerban et al. |
| 7,932,273 | B2 | | 4/2011 | Schmid et al. |
| 8,119,810 | B2 | | 2/2012 | Broeder et al. |
| 8,354,543 | B2 | | 1/2013 | Zerban et al. |
| 8,378,113 | B2 | | 2/2013 | Heddesheimer et al. |
| 8,399,678 | B2 | | 3/2013 | Gnad et al. |
| 8,471,033 | B2 | | 6/2013 | Filser et al. |
| 2003/0004181 | A1 | | 1/2003 | Hauel et al. |
| 2003/0181488 | A1 | | 9/2003 | Brauns |
| 2003/0211168 | A1 | | 11/2003 | Lynenskjold et al. |
| 2005/0103677 | A1 | | 5/2005 | Fuchsberger |
| 2005/0107438 | A1 | | 5/2005 | Radtke et al. |
| 2005/0234104 | A1 | * | 10/2005 | Schmid et al. ................. 514/338 |
| 2006/0183779 | A1 | * | 8/2006 | Brauns et al. ................. 514/338 |
| 2006/0247278 | A1 | | 11/2006 | Sieger et al. |
| 2006/0276513 | A1 | | 12/2006 | Hauel et al. |
| 2007/0185333 | A1 | | 8/2007 | Zerban et al. |
| 2009/0042948 | A1 | | 2/2009 | Sieger et al. |
| 2010/0087488 | A1 | | 4/2010 | Pop et al. |
| 2010/0144796 | A1 | | 6/2010 | Pop et al. |

(Continued)

FOREIGN PATENT DOCUMENTS

| DE | 10339862 A1 | 3/2005 |
| DE | 102005020002 A1 | 11/2006 |

(Continued)

OTHER PUBLICATIONS

International Search Report for PCT/EP2009/053469 mailed Jul. 7, 2009.

(Continued)

*Primary Examiner* — H. Sarah Park
(74) *Attorney, Agent, or Firm* — Michael P. Morris; Wendy A. Petka

(57) ABSTRACT

The invention relates to an improved process for preparing a new medicament formulation of the active substance dabigatran etexilate of formula I

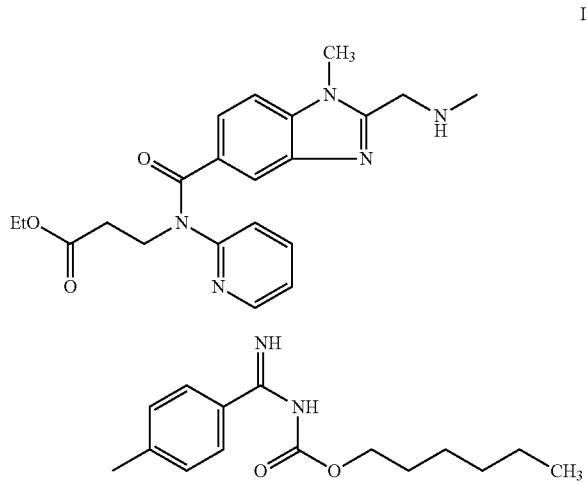

in the form of the methanesulphonic acid salt thereof, and this new medicament formulation as such.

17 Claims, No Drawings

(56) References Cited

U.S. PATENT DOCUMENTS

| | | |
|---|---|---|
| 2010/0210845 A1 | 8/2010 | Zerban et al. |
| 2011/0118471 A1 | 5/2011 | Filser et al. |
| 2011/0129538 A1 | 6/2011 | Landerer et al. |
| 2011/0275824 A1 | 11/2011 | Gnad et al. |
| 2011/0295018 A1 | 12/2011 | Heddesheimer et al. |
| 2012/0040384 A1 | 2/2012 | Stangier |
| 2012/0116089 A1 | 5/2012 | Broeder et al. |
| 2012/0276206 A1 | 11/2012 | Maier |
| 2013/0251810 A1 | 9/2013 | Landerer et al. |

FOREIGN PATENT DOCUMENTS

| | | |
|---|---|---|
| DE | 102005025728 A1 | 12/2006 |
| WO | 9837075 A1 | 8/1998 |
| WO | 03074056 A1 | 9/2003 |
| WO | 2005028468 A | 3/2005 |
| WO | 2008009639 A2 | 1/2008 |
| WO | 2008009640 A1 | 1/2008 |
| WO | 2009118321 A1 | 10/2009 |

OTHER PUBLICATIONS

International Search Report for PCT/EP2009/058900 mailed Sep. 10, 2009.

Mungall, Dennis, BIRB-1048 Boehringer Ingelheim, Current Opinion in Investigational Drugs, 2002 3(6) 905-907.

Stangier, Joachim, et al; The Pharmacokinetics and Tolerability of Dabigatran Etexilate, A New Oral Direct Thrombin Inhibitor, in Healthy Male Subjects; British Journal of Clinical Pharmacology (2007) vol. 64, No. 3 pp. 292-303.

U.S. Appl. No. 12/934,828, filed Nov. 23, 2010, Maier, Johann-Georg.

* cited by examiner

METHOD FOR MANUFACTURING MEDICINAL COMPOUNDS CONTAINING DABIGATRAN

The invention relates to an improved fluidised bed process for preparing a new medicament formulation of the active substance dabigatran etexilate of formula I

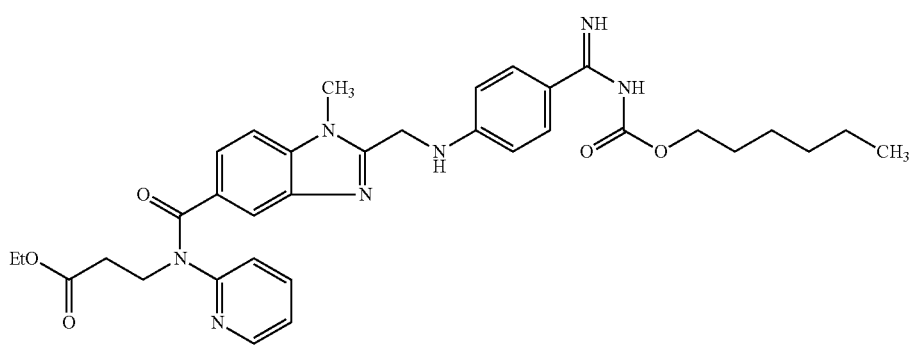

optionally in the form of the pharmaceutically acceptable salts thereof, as well as the new medicament formulation as such.

BACKGROUND OF THE INVENTION

The compound of formula 1 is known from the prior art and was first disclosed in WO98/37075. It is a potent thrombin inhibitor which can be used for example for the post-operative prevention of deep vein thromboses and in stroke prevention, particularly for preventing strokes in patients with atrial fibrillation. WO 03/074056 discloses the methanesulphonic acid addition salt of dabigatran-etexilate (ie: dabigatran etexilate methansulphonate) to be particularly useful.

The compound is usually administered orally. In particular, so-called pellet formulations may be used, as disclosed for example in WO 03/074056. These formulations are compositions, in which an active substance layer containing binder and optionally separating agent and surrounding a core material is applied to the substantially spherical core material, which consists of or contains a pharmaceutically acceptable organic acid. The core layer and the active substance layer are separated from one another by a so-called isolating layer. The schematic structure of an active substance formulation of this kind is shown in FIG. 1 of WO 03/074056.

The present invention relates to a process that can be used on an industrial scale for preparing active substance pellets containing dabigatran, which allows the formulation to be manufactured on a large scale. A further aim of the invention is to provide a process which allows the formulation to be manufactured with a reproducible quality.

According to WO 05/028468 the methansulphonic acid addition salt of dabigatran etexilate exists in different polymorphic forms. It is another aim of the invention to provide for a manufacturing process which allows the manufacture of a pharmaceutical formulation that contains only one polymorphic form of the active ingredient dabigatran etexilat methansulphonate.

DETAILED DESCRIPTION OF THE INVENTION

According to WO 05/028468 the methansulphonic acid addition salt of dabigatran etexilate exists in different polymorphic forms. Surprisingly it has been found that polymorph I of dabigatran etexilate methanesulphonate is advantageous over polymorph II in view of its crystallisation properties. This allows polymorph I to be easier isolated and handled in and after the manufacturing process of the active ingredient. According to the invention, polymorph I is therefore the preferred polymorph.

In principle, different polymorphic forms of a substance may be characterized by different properties (including but not limited to stability, efficacy, processing properties during manufacture etc). As a matter of principle it is, therefore, advisable to produce a pharmaceutical composition that contains essentially only one polymorph.

Consequently, the invention relates to manufacturing process which allows the manufacture of a pharmaceutical formulation that contains essentially polymorph I of the active ingredient dabigatran etexilat methansulphonate.

The process according to the invention is characterised by a series of partial steps. First, the core 1 is produced from pharmaceutically acceptable organic acid. Within the scope of the present invention tartaric acid is used to prepare the core 1. The core material 1 thus obtained is then converted into so-called isolated tartaric acid cores 3 by spraying on an isolating suspension 2. A dabigatran suspension 4 prepared subsequently is sprayed onto these coated cores 3 in one or more process steps by means of a coating process. Finally, the active substance pellets 5 thus obtained are 1 packed into suitable capsules.

The isolated tartaric acid cores 3 should have a uniform, quasi-spherical geometry. Moreover they should have only minor potential defects in the isolation caused by satellites. The so-called satellites are small particles adhering to the outside of the otherwise rounded pellets and detracting from the otherwise quasi-spherical geometry of the pellets. The ideally spherical shape and low surface roughness is of particular importance for acid-sensitive active substances such as for example dabigatran etexilate, in which defects in the isolation caused by satellites that have broken off or by the excessively rough surface of over-large particles of tartaric acid powder may lead to significantly impaired storage stability and hence durability of the finished product. For this reason, with acid-sensitive active substances it is also essential to apply the isolating layer as such with high reproducibility and consistently high quality.

The core 1 is prepared from tartaric acid particles with a particle size in the range from 0.2-0.8 mm, preferably 0.3-0.7 mm, particularly preferably 0.4-0 6 mm (determined by air jet screening) onto which a solution of tartaric acid and binder is sprayed. The following method is used to prepare the solution. Tartaric acid is first of all dissolved in water together with a suitable binder, preferably with acacia (gum arabic) at elevated temperature, preferably at a temperature in the range from 30-70° C., particularly preferably in the range from 40-60° C. Preferably, 0.1-0.3 kg, particularly preferably 0.15-0.25 kg, particularly about 0.2 kg acacia are used per kilogram of tartaric acid put in. The amount of water is preferably 0.6-1.0 kg, preferably 0.7-0.9 kg, particularly about 0.8 kg per kilogram of tartaric acid put in.

Preferably, according to the invention, first of all a clear solution of acacia in water is prepared at the above-mentioned temperature. Once this has been obtained, the tartaric acid is then added preferably at constant temperature and while stirring continues. After the addition has ended the mixture is stirred for at least 1 hour, preferably between 3 and 10, particularly preferably 4-8, particularly preferably 5-6 hours.

The solution thus obtained is sprayed onto tartaric acid particles with a particle size of 0.2-0.8 mm, preferably 0.3-0.7 mm, particularly preferably 0.4-0.6 mm The proportion of particles with the above-mentioned particle size should be at least 90%, preferably at least 95%, particularly preferably at least 97%. For this, the tartaric acid particles are placed in a suitable container. The container is preferably a pan in which the particles are mixed and moved about by the rotation of the pan. Various designs of pan are known in the art and may optionally also be referred to as drum coaters. On this subject reference is made for example to the disclosures of EP 80199, WO 83/03052, WO 95/19713 or WO 06/134133. Within the scope of the present invention pans that may be used in the process according to the invention are optionally also known as horizontal pans.

The acid gum solution prepared by the method described hereinbefore is then sprayed onto the particles kept moving by rotation.

Within the scope of the present invention the material supplied for spraying is optionally also referred to as the pellet bed. The term pellet is to be regarded as equivalent to the term particle or core within the scope of the present invention.

According to the invention, preferably 0.8-1.6 kg, particularly preferably 1.0-1.4 kg, particularly preferably 1.2 kg of the above-mentioned acid gum solution are sprayed on per kilogram of tartaric acid particles supplied.

The amount of supply air in the process according to the invention is dependent on the batch size. The standardised amount of supply air per kilogram of tartaric acid cores supplied according to the invention is preferably in the range from 0.5-2 ($m^3$/h)/kg, preferably 0.75-1.5 ($m^3$/h)/kg, particularly preferably 0.9-1.1 ($m^3$/h)/kg. By the amount of supply air is meant the amount of dry air introduced into the rotating pellet bed per hour.

If for example 1000 kg tartaric acid cores are placed in one batch, a standardised amount of supply air of 1.0 ($m^3$/h)/kg corresponds to an actual amount of supply air of 1000 $m^3$/h. The temperature of the supply air fed in for drying according to the invention is preferably below 90° C., particularly preferably below 80° C. Ideally the temperature of the supply air should be in the range from 35°-75° C.

The pellet temperature (the temperature of the pellet bed formed) according to the invention is preferably in the range from 30-50° C., particularly preferably 36-44° C., ideally 38-42° C.

The differential pressure is preferably 1-3 mbar, particularly preferably 1.5-2.5 mbar, particularly preferably 1.8-2.2 mbar. The differential pressure is the pressure difference between the pan pressure and ambient pressure. The pan should preferably be at reduced pressure so that no acid dust escapes.

Spraying is carried out at a defined spray rate. By the spray rate is meant the amount of acid gum solution that is sprayed onto the rotating pellet bed per hour. The spray rate is dependant on the batch size in the process according to the invention. The standardised spray rate according to the invention per kilogram of tartaric acid crystals supplied is preferably in the range from 0.2-0.4 (kg/h)/kg, preferably 0.25-0.35 (kg/h)/kg, particularly preferably 0.28-0.32 (kg/h)/kg. If for example 1000 kg tartaric acid crystals are placed in one batch, a standardised spray rate of 0.3 (kg/h)/kg corresponds to an actual spray rate of 300 kg/h.

After a first portion of the acid gum solution has been sprayed onto the tartaric acid particles of particle size 0.2-0 8 mm and the solution has been distributed by rotating the pan, fine tartaric acid powder is sprinkled onto the moist tartaric acid particles. This tartaric acid powder consists of fine tartaric acid particles with a particle size of <100, preferably <75, particularly preferably <50 microns (determined by air jet screening). The proportion of particles with the above-mentioned particle size should be at least 85%, preferably at least 90%, particularly preferably at least 94%. According to the invention preferably 0.4-1.2 kg, particularly preferably 0.6-1.0 kg, particularly preferably 0.8 kg of the above-mentioned tartaric acid powder are used per kilogram of tartaric acid particles supplied. After sprinkling with the above-mentioned tartaric acid powder the material for spraying is dried until a product temperature of about 30-50° C., preferably about 40° C. is reached. After this, the acid gum solution is sprayed on again.

To ensure the uniform formation of spherical particles, the spraying on of the acid gum solution and the sprinkling with tartaric acid powder are carried out alternately. The total amounts of acid gum solution and tartaric acid powder are supplied in at least 100, preferably 150 to 350, particularly preferably 200 to 300, particularly preferably about 250 batches of similar size and the process steps described hereinbefore are repeated a corresponding number of times.

Once the process has ended, the cores 1 obtained are dried. The drying is preferably carried out at a temperature of 50-70° C., preferably 55-65° C. over a period of 24-72 hours, preferably 36-60 hours.

After the preparation of the tartaric acid cores 1 so-called isolation of the core material is necessary. An isolating layer is applied around the tartaric acid core, preventing any interaction of active substance with tartaric acid core in the later product.

The core material is isolated by spraying an isolating suspension 2 onto the tartaric acid cores 1 obtained by the process described hereinbefore. To prepare the isolating suspension 2 ethanol is placed in the batch container and hydroxypropylmethylcellulose and dimethylpolysiloxane are added and dissolved therein with stirring, then talc is added and suspended.

The use of hydroxypropylmethylcellulose and talc has proved superior to the use of gum arabic and talc, for example. By using hydroxypropylmethylcellulose together with talc it is possible to produce an isolating layer of constant quality in a reproducible manner. This quality and reproducibility has been tested on an industrial scale.

To prepare the isolating suspension 2, preferably 0.04-0.06 kg, particularly preferably 0.046-0.05 kg hydroxypropylmethylcellulose are used per kilogram of ethanol. Besides the use of hydroxypropylmethylcellulose it has proved particularly preferable according to the invention to add dimethylpolysiloxane to the isolating suspension 2 to prevent foaming. The amount of dimethylpolysiloxane which is added with stirring to the preparation of the isolating suspension 2 is preferably 0.6-1.2 g, particularly preferably 0.8-0.9 g per kilogram of ethanol. Finally talc is added and suspended therein with stirring. Preferably 0.04-0.06 kg, particularly preferably 0.046-0.05 kg talc are used per kilogram of ethanol.

The isolating suspension 2 thus prepared is sprayed onto the previously prepared tartaric acid pellets 1 in a continuous spray process in a conventional horizontal coater. 0.5-0.8 kg, preferably 0.55-0.75 kg, particularly preferably 0.6-0.7 kg of isolating suspension are sprayed on per kilogram of tartaric acid cores 1 supplied.

The spraying is carried out at a defined spray rate. By the spray rate is meant the amount of isolating suspension 2 sprayed onto the pellets 1 per hour. The spray rate in the process according to the invention is dependent on the batch size. The standardised spray rate according to the invention is preferably in the range from 0.01-0.1 (kg/h)/kg, preferably 0.02-0.04 (kg/h)/kg, particularly preferably 0.025-0.035 (kg/h)/kg per kilogram of tartaric acid pellets 1 supplied. If for example 1200 kg tartaric acid cores are placed in one batch, a standardised spray rate of 0.027 (kg/h)/kg corresponds to an actual spray rate of 32 kg/h. If for example 600 kg tartaric acid cores are placed in one batch, a standardised spray rate of 0.035 (kg/h)/kg corresponds to an actual spray rate of 21 kg/h.

During this continuous process the cores are dried continuously with a supply of air at up to 70° C., preferably from 25-70° C.

By the amount of supply air is meant the amount of dry air that is introduced into the rotating pellet bed per hour. The amount of supply air in the process according to the invention is dependant on the batch size. The standardised amount of supply air according to the invention is preferably in the range from 1.0-2.5 ($m^3$/h)/kg. Preferably 1.2-2.0 ($m^3$/h)/kg, particularly preferably 1.40-1.85 ($m^3$/h)/kg per kilogram of tartaric acid cores 2 originally supplied. If for example 600 kg tartaric acid cores 2 are placed in one batch, a standardised amount of supply air of 1.83 ($m^3$/h)/kg corresponds to an actual amount of supply air of 1100 $m^3$/h. If for example 1200 kg tartaric acid cores 3 are placed in one batch, a standardised amount of supply air of 1.42 ($m^3$/h)/kg corresponds to an actual amount of supply air of 1700 $m^3$/h.

The pellets 5 containing active substance are prepared by spraying an active substance suspension 4 onto the isolated tartaric acid cores 3 obtained by the method described hereinbefore. The preparation of the active substance suspension 4 is of particular importance according to the invention as both the homogeneity and the temperature of the active substance suspension 4 are pertinent to the quality of the pellets containing the active substance.

The active substance suspension 4 is prepared using dabigatran etexilate methanesulphonate in the form of its polymorph I. Polymorph I is characterised inter alia by a melting point of $T_{mp.}$=180±3° C. (determined by DSC; evaluated using peak maximum; heating rate: 10° C./min). The targeted production of polymorph I is possible for example using the method described in WO 05/028468 (cf. particularly Example 1). Where the term active substance is used within the scope of the present invention, unless stated otherwise, this is to be understood as being a reference to polymorph I of dabigatran etexilate methanesulphonate.

In order to prepare the active substance suspension 4 isopropyl alcohol is taken and adjusted to a temperature range of 12-22° C. under a nitrogen atmosphere. Then hydroxypropylcellulose is sucked into the prepared substance using vacuum or circulatory dispersal with stirring. Preferably the preparation is carried out using a special dispersion device (rotor-stator principle; e.g. Ultra Turrax® made by Jahnke & Kunkel or CONTI TDS 4® made by Ystral GmbH). Circulatory dispersal denotes that the dispersion device is connected to the batch container and the prepared isopropyl alcohol is circulated through the disperser. The rotor-stator principle generates the suction vacuum required to suck in the solid. The liquid and solid enter the dispersing chamber by separate routes and are wetted therein during the suction process. As the process takes place during circulation, it is referred to as circulatory dispersal.

The batch container in which the process takes place is in turn provided with a mixer which achieves the optimum stirring action of the dabigatran etexilate suspension with low energy input (e.g. Visco Jet® stirring system made by Visco Jet GmbH or an air jet mixer). Furthermore, the batch container is optionally provided with a double jacket. Isopropyl alcohol is preferably used in substantially anhydrous form (99.5%). The hydroxypropylcellulose is sucked in by vacuum or circulatory dispersal at 2000-4000 rpm, preferably at 2900 rpm, and incorporated with stirring. The stirring performance of the mixer in the batch container is e.g. 600 rpm.

After 30-60 minutes the dissolving process is complete. Then the intake of the active substance dabigatran etexilate methanesulphonate and the excipient talc begins, again using vacuum or preferably circulatory dispersion.

As a result of the dispersion in the circulatory process it is possible to prepare the suspension 4 according to the invention significantly more rapidly than by using conventional stirring techniques.

Advantageously, the active substance is ground up before the preparation of the suspension. The preferred particle size distribution of the active substance is at an $X_{90}$ of less than 14 μm. The characteristic value $X_{90}$ denotes the median value of the particle size below which are found 90% of the quantity of particles with regard to the distribution by volume of the individual particles. The particle sizes may for example be determined within the scope of the present invention by laser diffraction (Fraunhofer diffraction).

There is then a stirring and swelling phase lasting 30 minutes during which the mixer is operated at a stiffing speed of 400-800 rpm, preferably 600 rpm. Then the suspension is dispersed for 3-10 minutes by the circulatory process at 2000-4000 rpm, preferably at 2900 rpm. The dispersing stirring cycle is optionally repeated up to six times.

To prepare the suspension 4, 0.05 to 0.5 kg, preferably 0.1 to 0.3 kg, particularly preferably 0.15-0.25 kg active substance are used per kilogram of isopropyl alcohol put in. The amount of hydroxypropylcellulose used is 0.01 to 0.1 kg, preferably 0.02 to 0.07 kg particularly preferably 0.03-0.05 kg, per kilogram of isopropyl alcohol put in. The amount of talc used is 0.005 to 0.07 kg, preferably 0.01 to 0.05 kg, particularly preferably 0.02-0.04 kg, per kilogram of isopropyl alcohol put in.

The ratio of active substance to hydroxypropylcellulose is preferably in the range from 3:1 to 7:1, preferably 4:1 to 6:1, particularly preferably about 5:1, with regard to the mass of the two constituents in the active substance suspension according to the invention. The ratio of active substance to talc is preferably in the range from 4:1 to 8:1, preferably 5:1 to 7:1, particularly preferably 6:1 to 6.5:1 with regard to the mass of the two constituents in the active substance suspension according to the invention.

The concentration of the active substance is preferably at 10-25% (w/w), preferably at 11-20% (w/w), particularly preferably at 12-19% (w/w) in the active substance suspension according to the invention. The total concentration of the constituents active substance, hydroxypropylcellulose and talc in the active substance suspension according to the invention is preferably 14-40% (w/w), preferably 15-30% (w/w), particularly preferably 16-25% (w/w).

Within the scope of the present invention, unless stated otherwise, concentrations are always given as percent by weight or mass percent.

Surprisingly it has been found that the temperature selected for the preparation of the suspension 4 has a decisive effect on the characteristics of the final product. In order to guarantee that the manufacturing process reproducibly leads to a product with a defined polymorphic form of the active substance, it turned out that the temperature should best be kept below 30° C. throughout the entire manufacturing process. If the suspension 4 is produced or even stored at too high a temperature, this may lead to a change in the polymorphic form of the active substance, which may have negatively affect the efficacy of the final formulation. Particularly preferably the temperature of the manufacturing process is in the range from 0-30° C., particularly preferably in the range from 5-30° C.

To prevent sedimentation, the suspension is stirred throughout the entire manufacturing process including the spray process. The stirring power of the mixer in the batch container is preferably 300-500 rpm, particularly preferably 400 rpm.

After it has been produced the active substance suspension 4 is stored at below 30° C. until further processing is carried out. Preferably the suspension 4 is processed further in the course of not more than 48 h. If the suspension is prepared and stored at 22° C., for example, it is preferably further processed within 60 hours.

In one aspect the present invention relates to a process for preparing a suspension 4 of the polymorph I of dabigatran etexilate methanesulphonate in isopropyl alcohol, which is characterised in that the temperature during the manufacture and storage of the suspension is always below 30° C., preferably in the range from 0-30° C., particularly preferably in the range from 5-30° C., the ingredients of the suspension being added by circulatory dispersion.

In another aspect the present invention relates to the suspension 4 of the polymorph I of dabigatran etexilate methanesulphonate in isopropyl alcohol, which may be obtained by the manufacturing process mentioned above.

In another aspect the present invention relates to the use of the suspension 4 of the polymorph I of dabigatran etexilate methanesulphonate in isopropyl alcohol as starting material for preparing a medicament formulation of dabigatran etexilate methanesulphonate.

In another aspect the present invention relates to the use of the active substance suspension 4 according to the invention as starting material for preparing a medicament formulation of dabigatran etexilate methanesulphonate, the suspension 4 having been reacted within 48 h at a storage temperature of less than 30° C.

In another aspect the present invention relates to the use of the active substance suspension 4 according to the invention as starting material for preparing a medicament formulation of dabigatran etexilate methanesulphonate, the suspension 4 having been reacted within 60 h at a storage temperature of less than 22° C.

To prepare the final active substance formulation 5 the active substance suspension 4 obtained by the above process is sprayed onto the isolated tartaric acid cores 3 described hereinbefore.

In another aspect the present invention relates to a process for preparing a medicament formulation of dabigatran etexilate methanesulphonate 5, characterised in that the active substance suspension 4 according to the invention is sprayed onto isolated tartaric acid cores 3.

In another aspect the present invention relates to a medicament formulation of dabigatran etexilate methanesulphonate 5, obtainable by spraying the active substance suspension 4 according to the invention onto isolated tartaric acid cores 3.

The subsequent preparation of the active substance pellets 5 according to the invention by the fluidised bed method is divided into three process steps:
1. preheating of the starter pellets 3
2. spraying phase (application of the active substance)
3. drying of the active substance pellets 5

These three process steps are carried out in a fluidised bed apparatus. By a fluidised bed apparatus is meant according to the invention that the product to be coated has a fluid, preferably air, flowing through it. The material put in is set in motion and kept in motion by this fluid, the nature of the movement being controlled by different equipment-specific inserts. Examples of suitable fluidised bed apparatus are GPCG (=Glatt Particle Coater Granulator), Precision Coater (Aeromatic), Kugelcoater (Hüttlin) or carried out using the Aircoater (Innojet). A so-called Wurster Coater as described for example in EP 0711 593 has proved particularly suitable for carrying out the fluidised bed process according to the invention.

For the preparation, the isolated tartaric acid starter pellets are placed in the product container, fluidised using process air and at the same time pre-heated. The process air current is generated by a ventilator provided downstream (vacuum method), but may also be generated by the pressure method. The supply air needed may be fed in directly from the outside air and heated or adjusted to a specific moisture level or water content by conditioning. Preferably the moisture level of the supply air is adjusted to 3 g/kg.

The product container is closed off by a perforated base plate in the supply air region. In the exhaust air region a filter cloth or screen insert prevents the pellets from escaping from the product chamber. Once the desired product temperature has been reached the spraying phase is started.

In the base plate there are one or more spray nozzles. The high degree of perforation in the base plate in the region of the spray nozzles causes the tartaric acid starter pellets 3 which are to be sprayed to be accelerated upwards and thereby sprayed with the active substance suspension according to the co-current principle. The pellets may be forcibly carried by an air current guided vertically through one or more tubes (Wurster-Coater or Precision-Coater), or they may follow a helical or toroidal motion of the process air in the product container and relaxation zone (Kugelcoater or Aircoater). Before and during the falling back of the sprayed pellets the volatile constituents are dried or eliminated. A uniform structure of the active substance layer is ensured by the circulating movement of the pellets. As the tartaric acid starter pellets are relatively small at the start of the process, a low spray pressure and a low spray rate are used to begin with. In the course of the process, the parameters of spray rate and spray pressure as well as supply air volume and supply air temperature are increased step by step to ensure optimum movement of the pellets and optimum product temperature.

In order to achieve good results in terms of homogeneity and uniformity of the active substance pellets 5 obtained, the product temperature, spray pressure, spray rate, temperature of supply air and amount of supply air in particular should be kept within specified ranges. Monitoring these parameters according to the present invention also ensures limited decomposition of the active substance, a reproducible content of active substance in the pellets 5, associated reduced spray losses and also reduced formation of multiples (clumps of several pellets). A reduced formation of multiples directly influences the yield as clumps would be separated off during the final screening of the active substance pellets 5.

By the product temperature is meant the temperature that prevails in the p, die in the pellet bed. The product container is first of all charged with the isolated tartaric acid pellets 3 described hereinbefore and the isolated tartaric acid pellets 3 are heated. They are preferably heated to a temperature of 30-50° C., preferably 30-48° C., particularly preferably 34-44° C. Once this temperature has been reached, the active substance suspension 4 described hereinbefore is sprayed on.

The temperature of the air supplied according to the invention is preferably below 90° C., particularly preferably below 80° C. Ideally the temperature of the supply air should be in the range from 40°-80° C., particularly preferably between 55-75° C.

By the spray pressure is meant the pressure of compressed air which is used for atomisation at the nozzle through which the active substance suspension 4 is sprayed on. The spray pressure according to the invention is preferably in the range from 1.0-4.0 bar, preferably 1.5-4.0 bar, particularly preferably 2.0-4.0 bar.

By the spray rate is meant the amount of active substance suspension 4 that is sprayed onto the fluid pellet bed per hour. The spray rate is dependant on the batch size in the process according to the invention. The standardised spray rate according to the invention per kilogram of isolated tartaric acid pellets 3 supplied is preferably in the range from 2-30 (g/min)/kg, preferably 4.5-30 (g/min)/kg, particularly preferably 6-26 (g/min)/kg.

If for example 270.56 kg tartaric acid pellets 3 are placed in a batch, a standardised spray rate of 7.39 (g/min)/kg corresponds to an actual spray rate of about 2000 g/min.

By the amount of supply air is meant the amount of dry air that is introduced into the fluid pellet bed per hour. The amount of supply air is dependant on the batch size in the process according to the invention. The standardised amount of supply air per kilogram of isolated tartaric acid pellets 3 supplied according to the invention is preferably in the range from 10-30 (m$^3$/h)/kg, preferably 14-30 (m$^3$/h)/kg, particularly preferably 18-28 (m$^3$/h)/kg.

If for example 270.56 kg tartaric acid pellets 3 are placed in one batch, a standardised amount of supply air of 20 (m$^3$/h)/kg corresponds to an actual amount of supply air of 5411 m$^3$/h.

After all the active substance suspension has been sprayed the active substance pellets are dried for a specified length of time, preferably 10-30 minutes, particularly preferably 20 minutes. The product temperature should preferably be adjusted to between 20 and 40° C. during the drying. Continuous fluidisation is also ensured during drying.

After the end of the process the product container is emptied gravimetrically and the dabigatran etexilate pellets are screened through a suitable screen, e.g. a vibrating screen (mesh size 1600 µm).

The amount of active substance suspension 4 sprayed on under the prevailing conditions depends not only on the active substance concentration in the suspension 4 but also on the batch size of the isolated tartaric acid pellets 3 supplied and the desired quantity of active substance per final active substance pellet (so-called charge). Particularly preferably the active substance charge per active substance pellet 5 is in the range from 15-50% (w/w). Particularly preferred active substance pellets 5 according to the invention have a charge of active substance of 20-45% (w/w), particularly preferably 36-42% (w/w).

If a particularly preferred active substance suspension 4 with an active substance concentration of about 15% (w/w) and an overall concentration of the constituents active substance, hydroxypropylcellulose and talc of about 25% (w/w) is used according to the invention, a desired charge of for example 40% of active substance per active substance pellet 5 with a supply of 1 kg of isolated tartaric acid pellets 3 requires the use of about 4.83 kg of active substance suspension 4 according to the invention. It may possibly make sense to use active substance suspension 4 in an excess of up to 5%, to compensate for any spray losses that may occur.

In the event of a greater charge of the isolated tartaric acid pellets 5 the total weight of the batch and, in the present case, in particular the volume naturally increases constantly during the spraying of the active substance suspension 4. A charge of for example 40% of the isolated tartaric acid pellets 3 with active substance leads to roughly a doubling of the total weight and an increase in bulk density by a factor of approx. 1.4 (i.e. an even greater increase in volume in relation to the mass) of the material for spraying 5. This sharp increase in the mass and particularly the volume of the material for spraying 5 may negatively affect the spray process in large industrial batches, as for example uniform drying of the spray material 5 can no longer be achieved easily or without complex technical procedures.

In another aspect the present invention relates to a medicament formulation of dabigatran etexilate methanesulphonate 5, obtainable by spraying the active substance suspension 4 according to the invention onto isolated tartaric acid cores 3 by the method described hereinbefore.

To eliminate any clumps that may have formed, the active substance pellets thus obtained are screened through screens of a defined mesh size. The mesh size selected naturally depends on the charging of the respective active substance pellets. For lower charges, closer-meshed screens may be used.

Finally, the active substance pellets obtained are packed into commercially obtainable capsules, preferably into commercially obtainable HPMC capsules.

The Examples that follow serve to illustrate the present invention in more detail.

Determining the Particle Sizes of Tartaric Acid by Air Jet Screening

Measuring Device and Settings:

Measuring device: Air jet screen, e.g. Alpine A 200 LS

Screens: As required

Weight put in: 10 g/screen

Duration: 1 min/screen, then 1 min each up to the maximum weight loss of 0.1 g

Preparation of Sample/Supply of Product:

The substance is transferred into a mortar and any lumps present are destroyed by intensive pounding. The screen with rubber seal and cover is placed on a balance, set to zero and 10.0 g of the pounded substance are weighed onto the screen.

The screen together with its contents, rubber seal and cover are placed on the device. The timer is set to 1 minute and the material is treated by air jet screening for this time. Then the residue is weighed out and documented. This process is repeated until the decrease in the weight of the residue after air jet screening is <0.1 g.

EXAMPLE 1

Preparation of the Starter Pellets 480 kg water are heated to 50° C. and 120 kg of acacia (gum arabic) are added with stirring in a conventional mixing container having a dished end and stirrer. Stirring is continued at constant temperature until a clear solution is obtained. Once there is a clear solution (usually after 1 to 2 hours) 600 kg tartaric acid are added with stirring. The tartaric acid is added at constant temperature while stirring is continued. After the addition has ended the mixture is stirred for about another 5 to 6 hours.

1000 kg tartaric acid are added to a slowly rotating (3 revolutions per minute) unperforated horizontal pan with a spraying and powder applying unit (e.g. Driamat 2000/2.5). Before spraying starts, a sample of the acid is taken for screening analysis. The acid in question is tartaric acid particles with a particle size in the range from 0.4-0.6 mm.

The acid rubber solution obtained by the above method is sprayed onto the tartaric acid particles thus provided. During the spraying, the quantity of air supplied is adjusted to 1000 $m^3/h$ and 35°-75° C. The differential pressure is 2 mbar and the speed of rotation of the pan is 9 revolutions per minute. The nozzles should be arranged at a distance of 350-450 mm from the filling.

The acid rubber solution is sprayed on by alternating with the following steps. After about 4.8 kg of the acid rubber solution has been sprayed onto the tartaric acid particles of particle size 0.4-0.6 mm and the solution has been distributed, about 3.2 kg tartaric acid powder are sprinkled onto the damp tartaric acid particles. The tartaric acid powder in question consists of fine tartaric acid particles with a particle size of <50 microns. In all, 800 kg tartaric acid powder are required. After the said tartaric acid powder has been sprinkled on and distributed the spray material is dried until a product temperature of about 40° C. is reached. This is in turn followed by the spraying on of the acid rubber solution.

These cycles are repeated until the acid rubber solution is used up. Once the process has ended the acid pellets are dried in the pan at 3 rpm for 240 minutes. To prevent caking after the drying has finished, an intermittent program is run at 3 rpm for 3 minutes every hour. In the present instance this means that the pan is rotated at 3 rpm for 3 minutes at intervals of one hour and then left to stand. The acid pellets are then transferred into a dryer. They are then dried at 60° C. over a period of 48 hours. Finally, the particle size distribution is determined by screen analysis. The particle size with a diameter of 0.6-0.8 mm corresponds to the product. This fraction should make up >85%.

EXAMPLE 2

Isolation of the Starter Pellets

To prepare the isolating suspension, 666.1 (347.5) kg of ethanol are placed in the mixing container and the hydroxypropylmethylcellulose (33.1 (17.3) kg) is added with stirring at approx. 600 rpm and dissolved. Then under the same conditions 0.6 (0.3) kg dimeticone are added. Shortly before use, talc (33.1 (17.3) kg) is added, again with stirring, and suspended.

The acid pellets 1200 (600) kg are poured into the coating apparatus (e.g. GS-Coater Mod. 600/Mod. 1200) and sprayed therein in the rotating pan with the isolating suspension described above in a continuous spraying process lasting several hours at a spraying rate of 32 kg/h for the 1200 kg mixture or 21 kg/h for the 600 kg mixture. The pellets are also dried continuously with an air supply at up to 70° C.

After the GS-Coater has been emptied, the isolated starter pellets are fractionated by screening. The product fraction with a diameter≤1.0 mm is stored and used further.

EXAMPLE 3

Preparation of the Dabigatran Etexilate Suspension

The batch container is inertised with nitrogen and nitrogen is passed over it throughout the entire process.

1028.325 kg of isopropyl alcohol are metered into the batch container. The temperature of the isopropyl alcohol must be between 12 and 22° C. before the addition of the 50.416 kg hydroxypropylcellulose (Klucel EF) can begin. The dispersing apparatus (CONTI TDS 4® made by Ystral GmbH) sucks the hydroxypropylcellulose into the prepared substance by circulatory dispersal. The stirring speed in the batch container is 600 rpm. After 30 min. a sample (100 ml) is taken from the hydroxypropylcellulose and passed through a 250 μm screen. If the solution is not clear and still contains recognisable particles, the dissolving process may be extended twice by 15 min. If the solution is clear and free from lumps, the addition of the active substance dabigatran etexilate methanesulphonate can be started. 252.006 kg of the active substance and 40.359 kg talc are sucked in successively by circulatory dispersal. After a stirring phase of 30 minutes the active substance suspension is dispersed for up to 10 minutes at 2900 rpm. Depending on the quality of the active substance suspension the dispersing-stirring cycle may be repeated up to 6 times. The quality of the active substance suspension is monitored by adding 100 ml of active substance suspension through a 500 μm screen after each dispersing-stirring cycle. The temperature of the suspension should not exceed 30° C. throughout the entire process. The storing and spraying temperature of the finished active substance suspension is adjusted to <18° C. If the suspension is stored at below 30° C., it should be further processed within at most 48 h. If for example the suspension is manufactured and stored at 22° C., it may should be further processed within 60 hours. If the suspension is stored for example at 35° C. it should be further processed within at most 24 h.

To prevent sedimentation, the active substance suspension is stirred throughout the entire manufacturing and spraying process.

EXAMPLE 4

Preparation of the Dabigatran Etexilate Active Substance Pellets

A fluidised bed apparatus is used (GPCG PRO 300). Spraying is carried out through nozzles 2.2 mm in diameter.

The product container is charged with 270.561 kg of the tartaric acid pellets obtained according to Example 2 and the pellet bed is heated up. Once a pellet bed temperature of 39° C. is reached, spraying starts. The suspension prepared according to Example 3 is sprayed on in seven 10-minute spray phases at increasing spray rates of 120 kg/h up to 420 kg/h.

The suspension is stirred constantly. The supply air temperature is not more than 75° C. The amount of supply air is about 7500 $m^3/h$. The spray pressure is in the range from 3-4 bar.

Then the pellets are dried in the product container at a supply air temperature of at least 20° C., at most 70° C. and with an amount of supply air of 6000 $m^3/h$ for a period of about 20 minutes.

The dried pellets are then screened through a vibrating 1 6 mm screen and stored in containers with desiccants until required for further processing.

EXAMPLE 5

Examples of Formulations

The following examples of formulations are then obtained from the active substance pellets obtained according to Example 4 by packing into hydroxypropylmethylcellulose capsules:

| Ingredient | amount [mg] per capsule | amount [mg] per capsule |
|---|---|---|
| active substance I | 86.48[1] | 126.83[2] |
| Acacia (gum arabic) | 4.43 | 6.50 |
| tartaric acid | 88.56 | 129.9 |
| hydroxymethyl-propylcellulose 2910 | 2.23 | 3.27 |
| dimethylpolysiloxane 350 | 0.04 | 0.06 |
| talc | 17.16 | 25.16 |
| hydroxypropylcellulose | 17.30 | 25.37 |
| HPMC capsule | 60[3] | 70[4] |
| Total | 276.2 | 387.1 |

[1]corresponds to 75 mg of free active substance base
[2]corresponds to 110 mg of free active substance base
[3]weight of capsule size is about 60 mg
[4]weight of capsule size is about 70 mg In another aspect the present invention relates to one of the above-mentioned medicament formulations as such.

In another aspect the present invention relates to a medicament formulation which contains 60-90 mg, preferably 70-80 mg, particularly preferably about 75 mg of dabigatran etexilate of formula I. In another aspect the present invention relates to a medicament formulation which contains 90-130 mg, preferably 100-120 mg, preferably 105-115 mg, particularly preferably about 110 mg of dabigatran etexilate of formula I.

In another aspect the present invention relates to a medicament formulation which contains 60-90 mg, preferably 70-80 mg, particularly preferably about 75 mg of dabigatran etexilate of formula I in the form of the polymorph I of its methanesulphonate. In another aspect the present invention relates to a medicament formulation which contains 90-130 mg, preferably 100-120 mg, preferably 105-115 mg, particularly preferably about 110 mg of dabigatran etexilate of formula I in the form of the polymorph I of its methanesulphonate.

In another aspect the present invention relates to a medicament formulation which also contains hydroxymethylpropylcellulose, besides dabigatran etexilate of formula I in the form of the polymorph I of its methanesulphonate.

In another aspect the present invention relates to a medicament formulation which also contains dimethylpolysiloxane besides dabigatran etexilate of formula I in the form of the polymorph I of its methanesulphonate.

In another aspect the present invention relates to a medicament formulation which also contains the constituents gum arabic, tartaric acid, hydroxymethylpropylcellulose, dimethylpolysiloxane, talc as well as hydropropylcellulose, besides dabigatran etexilate of formula I in the form of the polymorph I of its methanesulphonate.

In another aspect the present invention relates to a medicament formulation which contains exclusively the constituents gum arabic, tartaric acid, hydroxymethylpropylcellulose, dimethylpolysiloxane and talc as well as hydropropylcellulose, besides dabigatran etexilate of formula I in the form of the polymorph I of its methanesulphonate.

In another aspect the present invention relates to a medicament formulation which contains 60-90 mg, preferably 70-80 mg, particularly preferably about 75 mg of dabigatran etexilate of formula I, for the post-operative prevention of deep vein thromboses and in stroke prevention, particularly for preventing strokes in patients with atrial fibrillation. In another aspect the present invention relates to a medicament formulation which contains 90-130 mg, preferably 100-120 mg, preferably 105-115 mg, particularly preferably about 110 mg of dabigatran etexilate of formula I, for the post-operative prevention of deep vein thromboses and in stroke prevention, particularly for preventing strokes in patients with atrial fibrillation.

The invention claimed is:

1. A process for preparing a suspension 4 of a polymorph I of a methanesulphonic acid salt of dabigatran etexilate of formula I,

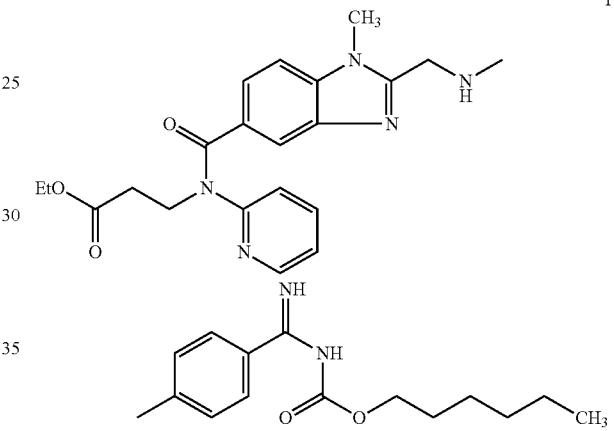

comprising the step of
mixing polymorph I of dabigatran etexilate methanesulphonate having a melting point of $T_{mp.}=180\pm3°$ C. (determined by DSC; heating rate: 10° C./min) with talc in a solution of hydroxypropylcellulose in isopropyl alcohol to form a suspension,
wherein the suspension is formed at a temperature between 12° C. and 22° C. by a circulatory dispersal process.

2. The process according to claim 1, wherein hydroxypropylcellulose is first dissolved in isopropyl alcohol to form the solution and then polymorph I of dabigatran etexilate methanesulphonate and talc are suspended in said solution.

3. The process according to claim 1, wherein 0.05 to 0.5 kg dabigatran etexilate methanesulphonate is used per kilogram of isopropyl alcohol.

4. The process according to claim 1, wherein 0.01 to 0.1 kg hydroxypropylcellulose is used per kilogram of isopropyl alcohol.

5. The process according to claim 1, wherein 0.005 to 0.07 kg talc is used per kilogram of isopropyl alcohol.

6. Suspension 4, made by the process according to claim 1.

7. Suspension 4 according to claim 6, wherein the concentration of polymorph I of dabigatran etexilate methanesulphonate (active substance) is 10-25% (w/w).

8. Suspension 4 according to claim 6, wherein the overall concentration of active substance, hydroxypropylcellulose and talc is 14-40% (w/w).

9. A process for preparing dabigatran etexilate methanesulphonate pellets 5, comprising the step of spraying suspension 4 according to claim 6 onto isolated tartaric acid cores 3 by a fluidised bed method.

10. The process for preparing dabigatran etexilate methanesulphonate pellets 5 according to claim 9, wherein the temperature of the pellets 3 is adjusted to 30-50° C.

11. The process for preparing dabigatran etexilate methanesulphonate pellets 5 according to claim 9, wherein the temperature of the supply air is below 90° C.

12. The process for preparing dabigatran etexilate methanesulphonate pellets 5 according to claim 9, wherein the standardised spray rate at which the suspension 4 is sprayed onto the tartaric acid pellets 3 is in the range from 4-45 g/min per kilogram of tartaric acid pellets 3 used.

13. The process for preparing dabigatran etexilate methanesulphonate pellets 5 according to claim 9, wherein the standardised amount of supply air is in the range from 10-35 ($m^3$/h) per kilogram of tartaric acid pellets 3 used.

14. Dabigatran etexilate methanesulphonate pellets 5, made by a process according to claim 9.

15. The process for preparing dabigatran etexilate methanesulphonate pellets 5 according to claim 9, wherein the temperature of the supply air is below 80° C.

16. The process for preparing dabigatran etexilate methanesulphonate pellets 5 according to claim 9, wherein the temperature of the supply air is between 40°-80° C.

17. The process for preparing dabigatran etexilate methanesulphonate pellets 5 according to claim 9, wherein the temperature of the supply air is between 55°-75° C.

* * * * *